(12) United States Patent
Benameur et al.

(10) Patent No.: US 6,217,899 B1
(45) Date of Patent: Apr. 17, 2001

(54) LIPOSOMES PREPARATION METHOD AND PLANT

(75) Inventors: Hassan Benameur, St Priest (FR); Andre Moes, Ans (BE)

(73) Assignee: Hassan Benameur, St. Priest (FR)

(*) Notice: Subject to any disclaimer, the term of this patent is extended or adjusted under 35 U.S.C. 154(b) by 0 days.

(21) Appl. No.: 09/180,046

(22) PCT Filed: Aug. 14, 1996

(86) PCT No.: PCT/BE96/00086

§ 371 Date: Oct. 29, 1998

§ 102(e) Date: Oct. 29, 1998

(87) PCT Pub. No.: WO97/06784

PCT Pub. Date: Feb. 27, 1997

Related U.S. Application Data

(60) Provisional application No. 60/002,369, filed on Aug. 15, 1995.

(51) Int. Cl.[7] .............................. A61K 9/127; A61K 9/133
(52) U.S. Cl. ............................. 424/450; 264/4.1; 264/4.3; 428/402.2
(58) Field of Search ................................ 624/450; 264/4.1, 264/4.3; 424/1.21, 9.321, 9.51, 417, 94.3; 436/829; 935/54; 428/402.2

(56) References Cited

U.S. PATENT DOCUMENTS

| 4,737,323 | | 4/1988 | Martin et al. . | |
|---|---|---|---|---|
| 5,000,887 | * | 3/1991 | Tenzel ................................. | 264/4.6 |
| 5,185,154 | | 2/1993 | Lasic et al. . | |

FOREIGN PATENT DOCUMENTS

| 119 020 | | 2/1984 | (EP) . |
|---|---|---|---|
| 2135647 | * | 9/1984 | (GB) . |
| 62180742 | | 8/1987 | (JP) . |
| 6-246150 | * | 9/1994 | (JP) . |
| 8059503 | | 3/1996 | (JP) . |
| WO 96/10393 | | 4/1996 | (WO) . |

* cited by examiner

*Primary Examiner*—Gollamudi S. Kishore
(74) *Attorney, Agent, or Firm*—Knobbe, Martens, Olson & Bear, LLP

(57) ABSTRACT

A process for the preparation of liposomes is described. The process includes the steps of formation of a lipid film on a ceramic filter, preferably an asymmetric ceramic filter, followed by hydration of the lipid film obtained. The liposomes thus formed are recovered. Multilamellar liposomes prepared by the process are also described.

12 Claims, 6 Drawing Sheets

LIPOSOMES PREPARATION METHOD AND PLANT

This is the U.S. national phase under 35 U.S.C. § 371 of International Application PCT/BE96/00086, filed Aug. 14, 1996, and claims the benefit of priority under 35 U.S.C. § 119(e) from Provisional Application Ser. No. 60/002,369, filed Aug. 15, 1995.

FIELD OF THE INVENTION

The present invention is related to a new liposomes preparation method and plant The present invention concerns also the liposomes populations obtained and their use.

BACKGROUND OF THE INVENTION

Liposomes are currently extensively studied as potential drugs or cosmetics carrier. A wide variety of liposomes preparations has been described and reviewed [1, 2, 6].

However, at the present time, most of the methods have not been scaled up from the laboratory level to the industrial production [3]. To ensure an optimal reproducibility of drug laden liposomes in vivo, the assessment of physico-chemical parameters (size, number of lipid bilayers, encapsulation efficiency, . . . ) characterizing the dispersion is essential.

In general, the mentioned parameters only refer to average data. But not only average values have to be considered; attention should also be paid to the homogeneity of the dispersions [3].

The preparation method in combination with the composition of the lipid mixtures and the nature of the aqueous dispersing solution decide upon morphology and homogeneity of the obtained liposome population and on their behaviour in vivo.

A well-defined preparation technique together with a fixed lipid composition and validated operating procedures are the key conditions to produce a liposome population with an acceptable reproducibility, suitable for pharmaceutical use.

STATE OF THE ART

In general, liposomes preparation includes two major steps: lipid hydration of a mixture of lipid with possibly liposoluble molecule and sizing to the desired particle size distribution. The difference between the various methods is the way in which these two steps are performed individually or how they are combined.

For convenience, these methods have been classified in three categories
mechanical dispersion methods such has hand-shaking and vortexing [2], sonication and use of a French press;
detergent-solubilizing dispersion methods [22];
solvent dispersion methods such as ethanol injection [12], ether infusion [15] and reverse-phase evaporation [14].

However, all these methods suffer from one or more drawback(s) in term of suitability for bulk manufacture for pharmaceutical applications (see tables 1 and 2 below).

In addition, for the pharmaceutical production at the industrial scale, a standard procedure to obtain lipidic vesicles in a specific size range is still missing.

Especially, liposome populations of large size liposomes (diameter >0.2 $\mu$m) with narrow size distributions are particularly difficult to produce.

TABLE 1

Characteristics of the liposome preparation methods

| Methods of preparation | Structure | Diameter ($\mu$m) | Volume Encapsulated ($\mu$l/$\mu$mol lipids) | % encapsulation (%) | Ref. |
|---|---|---|---|---|---|
| Hydration film | MLV | | | 1.8–8.5 | [4] |
| | | | 0.5 | 6 | [5] |
| | | 0.05–30 | 3 | | [6] |
| | | 0.4–5 | 4.1 | 5–15 | [7] |
| | | 1 | 1.4–1.8 | 9–27 | [8] |
| Ultrasonication of MLV | SUV | 0.02–0.05 | 0.2–1.5 | 0.1–1.0 | [9] |
| French press extrusion of MLV | SUV | 0.02–0.08 | 0.2–1.5 | 5–25 | [10] |
| Polycarbonates membranes extrusion of MLV | | | | | |
| 0.1 $\mu$m | SUV | 0.06–1 | 1–3 | 5–30 | [11] |
| 1–0.2 $\mu$m | MLV | 0.05–2 | 1.8–3.7 | 15–60 | [7] |
| Microfluidisation | SUV | <0.1 | 0.7–1.0 | 5–78 | [9] |
| Ethanol injection | SUV | 0.03 | | 0.5 | [12] |
| | | 0.12 | 0.4–1.5 | | [13] |
| Reverse phase evaporation | LUV | 0.1–1.0 | 7–11 | 30–68 | [14] |
| Ether infusion | LUV | 0.05–0.25 | 13–25 | 2 | [15] |
| Lyophilisation/ hydration | MLV | 0.02–0.2 | | 26–72 | [4] |
| Freezing/thawing (SUV) | LUV | 0.09 | | 25–30 | [16] |
| Congelation/ decongelation (MLV) | MLV | | 2–5 | 31–89 | [17] |
| Elimination of detergent | LUV | 0.6 | | 12 | [18] |
| | | 0.1 | 2.4 | 12 | [19] |
| | | 0.04–0.18 | 1.75–2.4 | | [20] |
| | | 0.2–0.3 | 6–7.4 | 22 | [21] |
| | SUV | 0.037 | 0.47 | | [22] |

TABLE 2

Advantages and inconveniences of the liposome preparation methods

| Preparation methods | Advantages | Inconveniences |
|---|---|---|
| Thin lipid film hydration by mechanical shaking (MLV) | Simple, rapid | Poor encapsulation efficiency Heterogeneous dispersion of MLV No upscaling feasibility |
| Ultrasonic irradiation (SUV) | Small liposomes (20 nm diameter) Homogeneity | Poor encapsulation efficiency Contamination by titane particles Production of aerosols Warming and lipid degradation can occur No upscaling feasibility |
| French press extrusion | Simple, reproducible, non aggressive High concentration of lipids can be used High encapsulation efficiency Scaling-up | Not economical Need the preparation of MLV Poor encapsulation efficiency |
| Extrusion through polycarbonate membranes | Rapid and reproducible Homogeneity High concentration of lipids High encapsulation efficiency | Need the preparation of MLV Only small volumes can be used |

TABLE 2-continued

Advantages and inconveniences of the liposome preparation methods

| Preparation methods | Advantages | Inconveniences |
|---|---|---|
| Microfluidisation | High encapsulation efficiency Scaling-up | Need the preparation of MLV Not economical |
| Organic solvent replacement Ethanol injection | Homogeneity Simple, rapid Scaling-up | Poor encapsulation efficiency |
| Reverse phase evaporation | High encapsulation efficiency | Lipids exposed to ultrasonic and solvents Complicated technic Low solubility in the organic solvents No upscaling feasibility |
| Ether infusion | High encapsulation efficiency Scaling-up | Poor encapsulation efficiency Lipids exposed to high temperature and solvents Heterogeneity |
| Lyophylisation/ rehydration | High encapsulation efficiency Simple Scaling-up Stability of the preparation | Heterogeneity Need the preparation of SUV |
| Freezing/thawing (MLV) | High encapsulation efficiency Rapid | Need the preparation of SUV |
| Freezing/thawing (SUV) | Process simple and rapid | Need the preparation of SUV Difficult to prepare in the presence of neutral phospholipids, sugar and high concentration of divalent ions |
| Removal of detergents | Homogeneity Smooth condition | Low encapsulation efficiency Lengthy process Difficulty to remove the detergent |

At the present time, the most direct methods for producing liposomes population on a large scale are based on high-shear homogenization. The major drawback of this method is that it allows only the production of small liposomes (<0.2 $\mu$m) with a relatively narrow size distribution.

For the production of large multilamellar liposomes (>1 $\mu$m), the lipid film hydration method can be used. However, said method is difficult to scale up due to the small surfaces available to dry the thin lipid film before the hydration step, which leads to the formation of vesicles characterized by large size distributions [3].

Nowadays, no method is available for large scale production of unilammelar or oligolamellar liposomes (i.e., consisting of a few bilayers) with a narrow size distribution in the range of 0.2–1 $\mu$m.

Usually, when the thin lipid film hydration method is applied, the particles size distribution of the liposomes produced is much broader and in many cases, the liposome population is bi- or even polymodal.

However, it is known that the size of the liposome particles is essential for their therapeutical use. For instance, according to their size, particles could reach different sites in the respiratory system. The table 3 represents the different sites reached by the particles according to their size.

TABLE 3

| Particle mean diameter size ($\mu$m) | Deposit |
|---|---|
| >100 | No deposit possible |
| >10 | Nasal cavity |
| >5 | Trachea, bronchus |
| >1 | Alveolus |
| >0.1 | Stable particles - low deposit |
| <0.1 | Important deposit |

Therefore, for some specific therapeutical uses, it is very important to provide a liposomes population having a very narrow size distribution. In addition, if the distribution of the liposomes population is homogeneous, it is possible to obtain a reproducible and reliable pharmaceutical composition with liposomes having a specific encapsulation efficiency of a specific active compound.

The U.S. Pat. No. 4,737,323 describes a method of producing a suspension of liposomes which have approximately an uniform size and a selected average size, said method comprising the step of providing a suspension of heterogeneous size liposomes containing a substantial proportion of liposomes having a size greater than 1.10 $\mu$m in size and the step of passing the suspension under pressure through an asymmetric ceramic filter whose inner surface pores size is greater than the desired average liposomes size. Therefore, the plant and the method according to the invention propose the use of said asymmetric ceramic filter only for the filtration of already prepared liposomes.

In addition, the above described laboratory preparation methods are difficult to adapt in order to obtain liposomes in a single vessel, in large quantities and under conditions which are adaptable to commercial production. Indeed, the liposomes are traditionally formed at the evaporation surface of balloon flasks. However, the traditional surface area of a 100 l balloon flask is around 1 m$^2$, which could roughly increase of 20% if microglass beads are added in the flask.

In the U.S. Pat. No. 5,028,297, it has been proposed to increase said evaporating surface by providing an evaporating apparatus for conducting batch processes for the formation of an amphiphilic lipid film, and the vesiculation of the film in an aqueous phase. Said device comprises a rotor blade secured to a rotable shaft which is disposed in a chamber where the liposomes are prepared. However, said complicated and expensive method and device do not increase enough the surface area for the production of liposomes, and does not guarantee the homogeneity of the liposomes population produced. Indeed, in all the above-described methods, it is necessary to have a further step for the caliberation of the liposome population obtained. Said calibration method does comprise a filtration and/or extrusion through a membrane or a ceramic filter. Therefore, said additional step will increase the complexity of the plant and does not guarantee the sterility of the obtained product. The extrusion and/or the filtration step is also used for the purification of the obtained liposomes.

AIMS OF THE INVENTION

The present invention aims to provide a new liposomes preparation method and plant which do not present the drawbacks of those of the state of the art.

The main aim of the invention is to provide a rapid, simple, reproducible, reliable and not expensive preparation method and plant.

Another aim of the invention is to provide a preparation method and plant which allow the liposomes production at the industrial scale and may satisfy the following requirements:

satisfying quality and sufficient availability of lipids and raw materials;

development of quality control and in process control procedures;

sterility;

apyrogenicity;

easy scaling up of liposomes production from the laboratory to the pilot plant, then to the industrial manufacturing process;

reproducibility of production process in term of size distribution, encapsulation efficiency and release pattern.

A further aim of the present invention is to provide also a liposomes population which is reproducible, reliable and which has a specific narrow sizing, preferably in the range of 0.2 to 1 µm, which is also sterile and pyrogen-free.

SUMMARY OF THE INVENTION

The present invention concerns a preparation method of liposomes comprising the step of a lipid film formation on a ceramic filter(may be a symetric or asymetric filter) An asymetric ceramic filter means that the pores size is decreasing from the innner side of the ceramic filter to the external side. If the ceramic filter is symetric, the pore size is not modified. The lipid film formation comprise a lipid or mixture of lipid such as phospholipids and/or cholesterol and possibly a lipophilic active ingredient.

Preferably, said preparation process comprises also the step of hydration of the lipid film obtained. Said hydration step is obtained by the use of aqueous medium (preferably, a buffer) in which hydrophilic drugs are possibly dissolved. The preparation process may also comprise a back-flushing step of an aqueous medium and recirculation of the obtained liposomes. In addition, the preparation process may also comprise a filtration and/or extrusion step which could be done upon a membrane or a ceramic filter, preferably an asymetric ceramic filter.

The various steps of the preparation process according to the invention could be adapted by a man skilled in the art according to the various raw materials used. The lipid film formation on the ceramic filter is advantageously obtained by a mixture of lipid and possibly a lipophilic drug dissolved in an organic solvant such as dichloromethane ($CH_2Cl_2$) or a mixture of organic solvents, which will be dried onto the surface of the ceramic filter after removal of the solvent.

Preferably, said lipid solution is filtered before the step of film formation on the ceramic filter, preferably through a PTFE 0.2 µm membrane. The other step of the preparation method will be described hereafter in detail.

The present invention concerns also a plant for the preparation of liposomes which comprises a ceramic filter, disposed in a liposomal reactor wherein the liposomes are formed. Said ceramic filter may be a symetric or asymetric ceramic filter.

Advantageously, said ceramic filter is an asymetric porous ceramic rod, preferably made of a silicon carbide matrix. Said cylindric rod comprises a plurality of main channels present into the length of the rod and microchannels disposed perpendicularly to said main channels, said microchannels having a narrow pores size. Advantageously, the pores size are comprised between 1 and 200 µm, preferably between 8 and 100 µm.

In the plant according to the invention, the ceramic rod is maintained in the centre of the liposomal reactor by a O-ring or by any other suitable device.

The plant according to the invention comprises also lipid and aqueous tanks connected to the liposomal reactor. The plant according to the invention may comprise several liposomal reactors disposed in parallel and may work in a continuous or semi-continuous way.

The plant comprises also means for the back-flushing of the acqueous medium into the liposomal reactor and means to obtain recirculation of the liposomes. Said liposomes may recirculate in a recycling holding tank A plant based upon the recirculation of the liposomes formed comprises also control means such as a flow indicator, a volumetric pump, various filters and pump units in order to control the pressure into the plant.

The present invention concerns also a liposomes population which is preferably obtained by the method according to the invention and/or by the use of the plant according to the invention.

A "liposomes population" means a dispersed distribution of liposomes of various sizes but with a specific liposomes mean diameter size and a specific standard deviation.

The liposomes population according to the invention comprises preferably a narrow mean diameter size in the range of 0.1 to 0.5 µm, preferably from 0.2 to to 1 µm and a ratio standard deviation/average mean diameter of the liposome population which is comprised between 0.1 and 20%, preferably between 8 and 15%:

Said liposomes may comprise lipophilic and/or hydrophilic active ingredients such as pharmaceutical products, cosmetics, metallic compounds, markers for diagnostic, . . . .

The present invention concerns also the Ceramic filter wherein a lipid film has been deposited and the kit comprissing said ceramic filter wherein the lipid film has been deposited. Said kit is a laboratory kit which comprises a liposomal reactor with said ceramic filter ready to use.

BRIEF DESCRIPTION OF THE DRAWINGS

The FIG. 1 represents a schematic view of the plant according to the invention.

The FIGS. 2 and 3 represent details of the plant according to the invention.

Figure 4A:
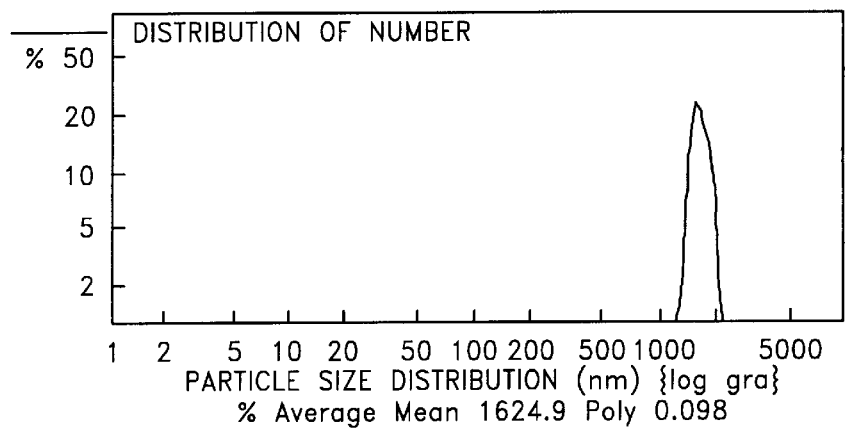
Figure 4B:
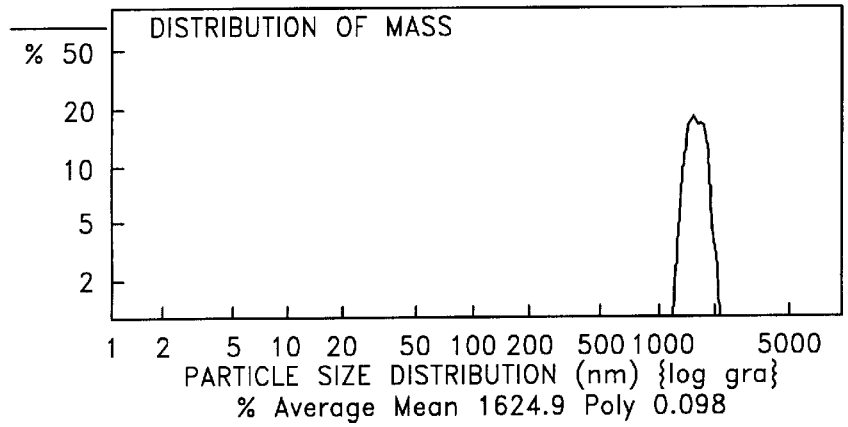
Figure 4C:
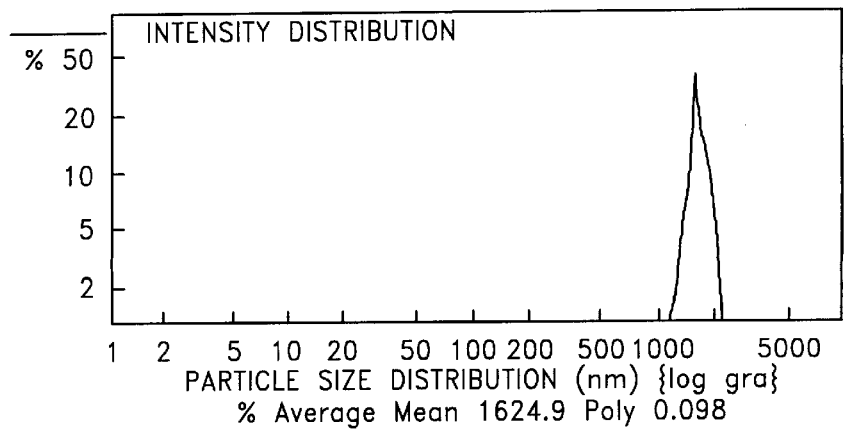

The FIG. 4 represent the particles size distribution of the liposomes population obtained by the method according to the invention.

Figure 5B:
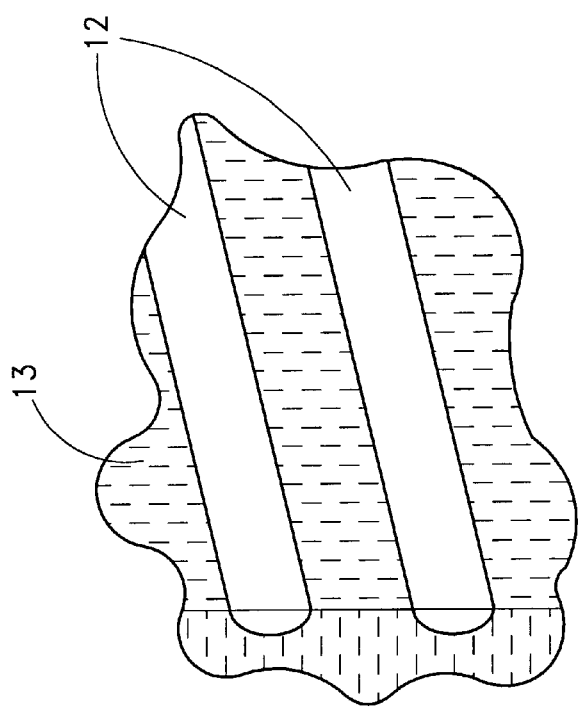
Figure 5A:
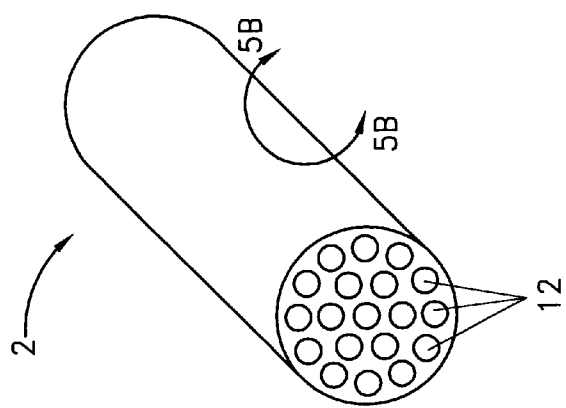
Figure 5C:
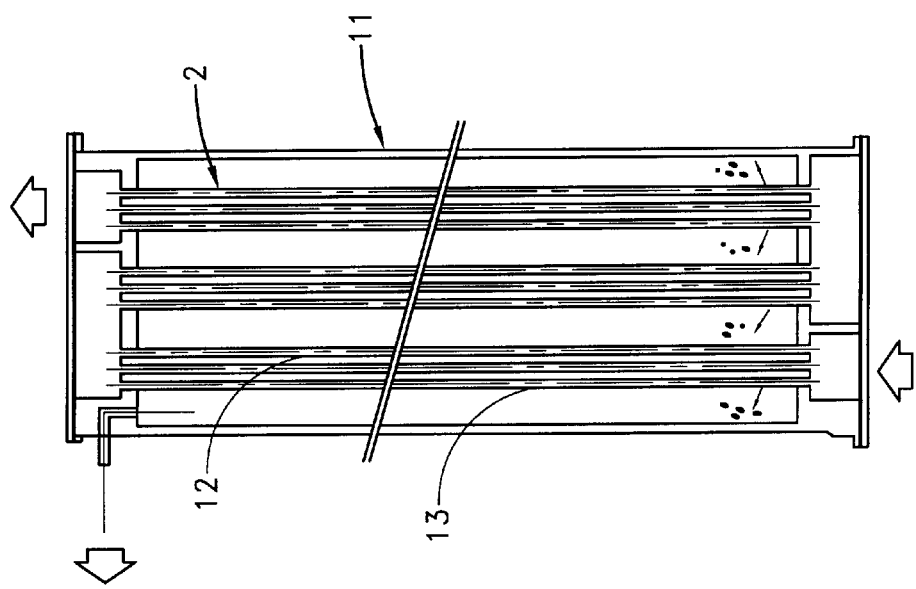

The FIG. 5 represents a schematic view of the ceramic matrix used in the plant according to the invention.

DESCRIPTION OF THE INVENTION

Figure 1:
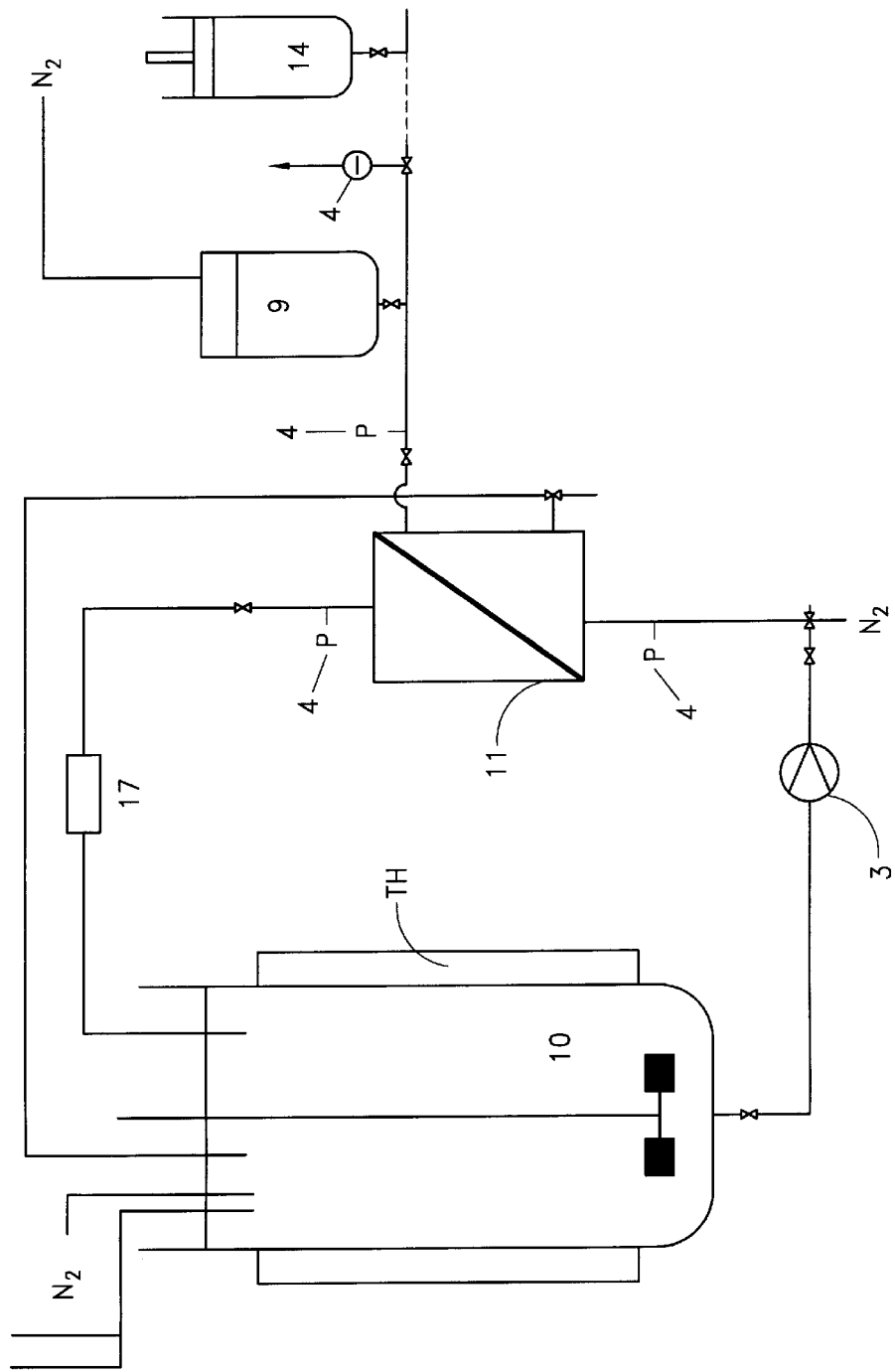

The production plant 1 described in the FIG. 1 is a liposomes production plant which comprises a liposomal cross-flow reactor 11 wherein the liposomes are formed, a pump unit 3, pressure indicators 4 (inlet and outlet), a flow indicator 17 a vacuum pump 6, a PTFE pipe, and an inox filter unit 8 (0.2 µm PTFE membrane), a lipid 9 and an aqueous 10 tanks.

The plant comprises also means 14 which are used to obtain a back-flushing an aqeous medium into the liposomal reactor 11 and means (3, 17) such as flow indicator, pumps . . . for the recirculation of the liposomes formed.

In the plant 1 according to the invention, the liposomal reactor 11 comprises an asymetric ceramic filter 2.

The ceramic filter is preferably an asymetric porous ceramic rod made for instance of a silicon carbide matrix and sold under the trademark µ-kerasep$^R$ by TECH-SEP,.

Said ceramic rod 2 as represented in the FIG. 5 comprises a plurality of main channels 12, present into the length of the cylindric rod. Said rod comprises also, preferably disposed perpendicularly to the main channels, microchannels 13 with narrow pores size. The characteristics of a suitable ceramic filter rod are
length: 900 mm
diameter: 25 mm
diameter of the 19 main channels: 2.5 mm
void volume: 90 ml (30%)
pores size: 8–100 µm The advantages of the use of said ceramic filter is the great surface area obtained, the use of an inert material having a high chemical resistance and a high mechanical strength, and which is easy to scale up by modular assembly. Preferably, the plant comprises various liposomal reactors 11 disposed in parallel.

At the laboratory scale, the capacity of the production plant 1 used is 100 ml of liposomes dispersions containing 10 mg lipids/ml.

By increasing the volume of the liposomal reactor 11, the production capacity can be easily increased up to 1–10 l. Even a scaled-up production plant for industrial batches of 100–200 l of highly concentrated liposomes can be used.

The method of liposomes production is based on the physical dispersion of lipids in aqueous media which leads to the spontaneous formation of phospholipid bilayers. This method can be divided in three steps The first step corresponds to the classical evaporated lipid film method.

A. Film formation

Lipids (phospholipids, cholesterol), and possibly lipophilic drugs are solubilized in the organic solvent.

Figure 2:
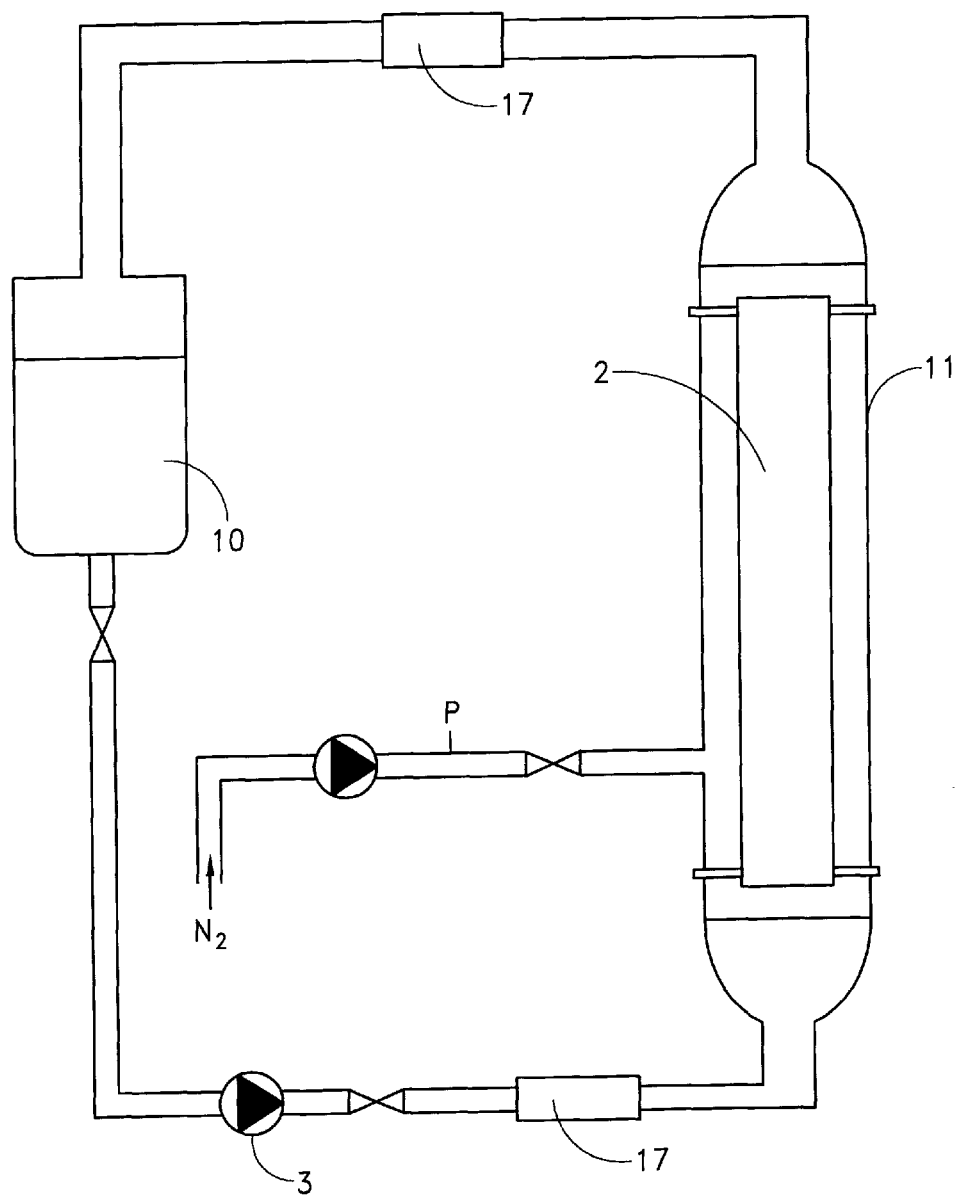
Figure 3:
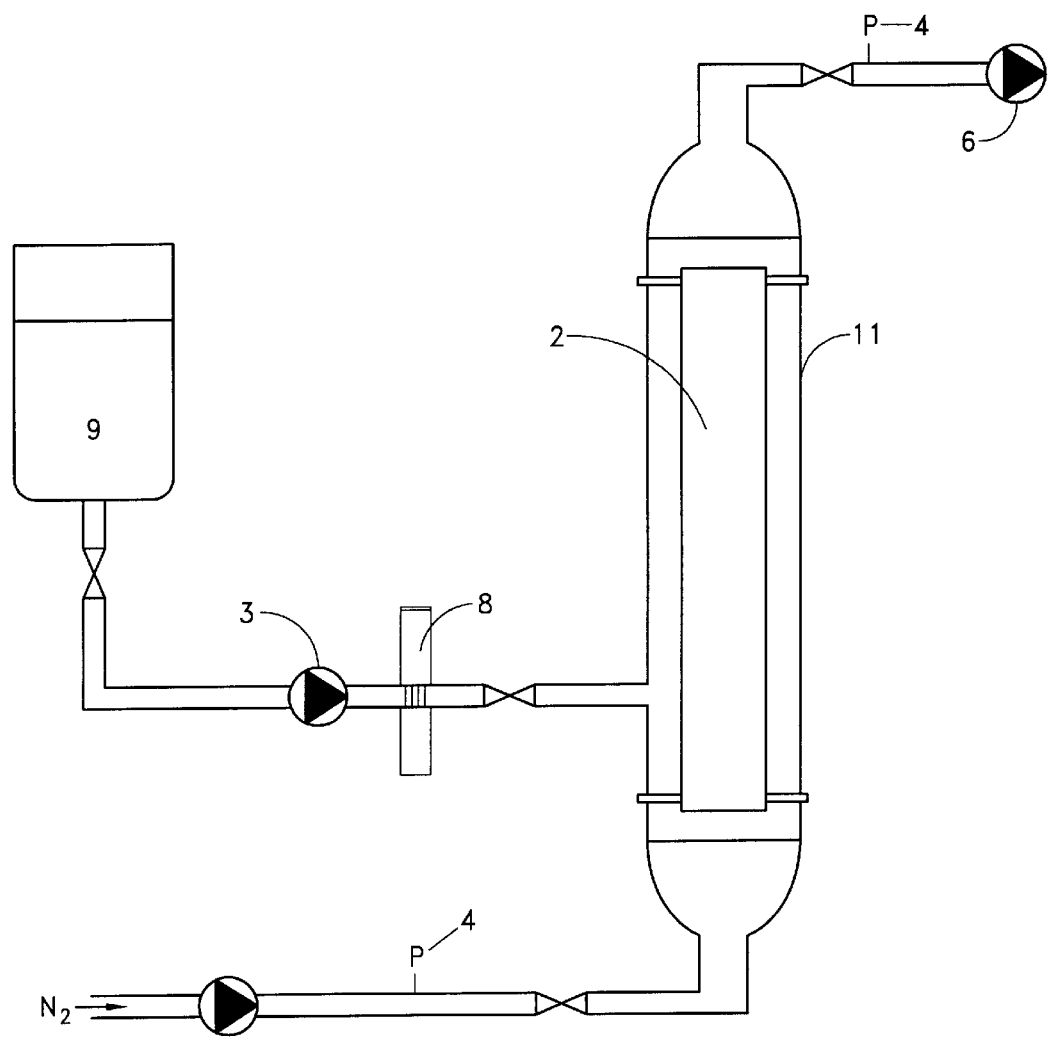

For instance, the lipid solution comprises 4 g of lipids: 3 g of Egg-Phosphatidylcholine (EPC) and 1 g of cholesterol (CH) dissolved in 50 ml of dichloromethane ($CH_2Cl_2$) in the lipid tank 9 (see FIGS. 1 and 2). This lipid solution is filtered (0.2 µm PTFE membrane) and transferred to the liposomal reactor 11 with the help of the membrane pump unit 3.

A back pressure is applied by a filtered inert gas (e.g. nitrogen) at relatively low pressure to keep the lipids solution into microchannels 13 of the ceramic filter. This solution is dried onto the surface of the asymetric ceramic filter 2 after removal of the solvent under reduced pressure. The drying process is carried out by evaporation of the dichloromethane in a nitrogen stream under reduced pressure.

The residual dichloromethane is removed from the dry lipid film under vacuum overnight. The excess pressure and solvent is removed by vacuum pump. This first step corresponds to the classical evaporated lipid film method.

As viscosity of the lipid solution used in low, said method does not need the use of high pressure and the energetic power used in said process is low. The plant comprises also a temperature control system.

B. Hydration

Hydration of the lipid film deposited on the asymetric ceramic filter 2 is performed with an appropriate aqueous medium (buffer) in which hydrophilic drugs are possibly dissolved.

The hydration of the lipid film by the buffer forms the liposomes which are at the same time "extruded" from the ceramic filter. To control this phenomena, a pressure is maintained in the liposomal reactor. When the liposomes are formed, the buffer is removed by the decreasing said pressure.

The method may comprise also a back-flushing step and recirculation of the liposome formed. The lipids dried onto the ceramic filter 2 are dispersed by addition of the aqueous medium (red ponceau 0.1 mg/ml phosphate buffer pH 7.4) by back-flushing and recirculation. During this step, multi-lamellar liposomes (MLV) with a narrow vesicle size distribution are formed. The ponceau red (Mw 760) was used as a water-soluble marker for liposomal entrapment studies (.1) The lipids swell and peel off from the ceramic filter 2 to form small multilamellar vesicles as shown by microscopy. These vesicles are characterized by a narrow size distribution as measured by light scattering. SMLVs with a mean diameter 1500 nm and narrow size distribution (see the FIG. 4) are produced thanks to the recirculation of the liposome dispersion through the asymetric ceramic filter 2 which is asymmetric (pore size 8 µm to 100 µm; see the FIG. 5). The operating process conditions (transmembrane pressure, cross-flow rate) are easily controlled and optimized. Five batches successfully produced are described in the FIG. 4 and in the table 4.

C. Extrusion and purifiation

Removal of unencapsulated drugs is often required when encapsulation is uncomplete. Several techniques can be used for that purpose. In the present case, a liposomal purification is carried out using the tangential microfiltration mode. A new calibration of the liposomes and/or transformation of MLV into SUV can be obtained by extrusion or filtration through a modified ceramic membrane or filter of desired pore size as above described.

Analytical determinations were performed on the different final product batches. The ponceau red encapsulation level was determined by colorimetry after extraction of the lipids by the Bligh-Dyer method [1]. The phospholipid was assayed by the method of Steward [1]. The liposomal size and the vesicle size distribution were determined by laser light scattering (Malvern).

The results obtained for five batches are shown in the table 4. The mean encapsulation level of ponceau red in the small MLV is 10%. These data are in accordance with those found in the litterature for the water-soluble compounds entrapped by liposomes prepared by the thin film method [1].

Lipophilic compounds, on the other hand, are encapsulated with 100% efficiency if they are not present in quantities which overwhelm the encapsulation capacity of the lipid bilayer.

Amongst the advantages of this new method of production of liposomes is the narrow size distribution of the SMLVs (mean diameter: 1500 nm) obtained and the high recovery level of lipids from the ceramic filter (90%) obtained.

TABLE 4

Analysis measurements before production

| Lot No. | EPC (mg/ml) | CH (mg/ml) | RP (mg/ml) |
|---|---|---|---|
| 94G05 | 30.250 | 11.560 | 0.116 |
| 94G28 | 29.440 | 11.480 | 0.118 |
| 94H02 | 29.600 | 11.650 | 0.100 |
| 94H08 | 29.260 | 11.560 | 0.100 |
| 94H18 | 10.083 | 3.853 | 0.100 |

Analysis measurements after production

| Lot No. | EPC (mg/ml) | CH (mg/ml) | RP (mg/ml) | % encaps. | % encaps (mg RP/ mg EPC) | % rendement | Size (nm) |
|---|---|---|---|---|---|---|---|
| 94G05 | 27.982 | N.D. | 0.012 | 10.3 | 0.043 | 92.5 | 1505 |
| 94G28 | 24.581 | N.D. | 0.011 | 9.0 | 0.043 | 83.5 | 1730 |

TABLE 4-continued

| | | | | | | | |
|---|---|---|---|---|---|---|---|
| 94H02 | 26.890 | N.D. | 0.014 | 14.2 | 0.053 | 90.8 | 1400 |
| 94H08 | 25.487 | N.D. | 0.010 | 10.0 | 0.039 | 87.1 | 1206 |
| 94H18 | 6.400 | N.D. | 0.007 | 6.8 | 0.107 | 63.5 | 1720 |
| <M> | 26.235 | N.D. | 0.012 | 10.9 | 0.045 | 88.5 | 1512 |
| σ | 1.503 | N.D. | 0.002 | 2.3 | 0.006 | 4.0 | 222 |
| CV | 5.7 | N.D. | 15.8 | 21.0 | 12.9 | 4.5 | 14.7 |

REFERENCES

[1] New R.R.C., *Liposomes, A Practical Approach*, Rickwood D., Hames B. M., ed. New York: IRL Press, Oxford University Press (1990)

[2] Bangham A. D. et al., *J. Mol. Biol.* 13, pp. 238–252 (1965)

[3] Martin F. J., *Pharmaceutical manufacturing of liposomes* in Praveen Tyle ed. Specialized Drug Delivery Systems; Marcel Dekker; New York and Basel, pp. 267–316 (1989)

[4] Kirby C. et al, *Biotechnology*, pp. 979–984 (1984)

[5] Cullis P. R. et al., *Liposomes as pharmaceuticals*, in Ostro M. J., ed. Liposomes from biophysics to therapeutics, pp. 39–72; Marcel Dekker; New York (1987)

[6] Lichtenberg D. te al., *Methods Biochem. Anal.* 33, pp. 337–462 (1988)

[7] Olson F. et al., *Biochim. Biophys. Acta* 557, pp. 9–23 (1979)

[8] Mayhew E. et al., *Biochim. Biophys. Acta* 775, pp. 169–174 (1984)

[9] Szoka F. C. et al., *Annu. Rev. Biophys. Bioeng.*, pp. 467–508 (1980)

[10] Lekkes I., *The use of French Pressed vesicles for efficient incorporation of bi oactive macromolecules and carriers in vitro and in vivo*, in Gregoraidis G., ed. Liposomes Technology, pp 51–65; C.R.C. Press: BOCa Raton Florida (1984)

[11] Hope M. J. et al., *Biochim. Biophys. Acta* 812, pp. 55–65 (1985)

[12] Batzri S. et al., *Biochim. Biophys. Acta* 298, pp. 1015–1019 (1973)

[13] Kremer J. M. H. et al., *Biochemistry* 16, pp. 3932–3935 (1977)

[14] Szoka F. C. te al., *Proc. Natl. Acad. Sci. USA* 75, pp. 4194–4198 (1978)

[15] Deamer D. et al., *Biochim. Biophys. Acta* 448, pp. 629–634 (1976)

[16] Bick U., *Arch. Biochim. Biophys.* 212, pp. 186–194 (1981)

[17] Mayer L. D. et al., *Biochim. Biophys. Acta* 817, pp. 193–196 (1985)

[18] Kagawa Y. et al., *J. Biol. Chim.* 246, pp. 145–149 (1971)

[19] Enach H. G. et al., *Proc. Natl. Acad. Sci. USA* 76, pp. 145–149 (1979)

[20] Zumbruchl O. et al., *Biochim. Biophys. Acta* 640, pp. 252–262 (1981)

[21] Nimms L. T. et al., Biochemistry 20, pp. 833–840 (1981)

[22] Brunner J. et al., *Biochem. Biophys. Acta* 455, pp. 322–331 (1976)

[23] Taslma H. et al., *Preparation Pharm. Tech. Int.*, pp. 24–33 (1992)

What is claimed is:

1. A process for the preparation of liposomes, comprising the steps of:

forming a lipid film on a surface of a ceramic filter, said ceramic filter being a porous ceramic rod comprising a plurality of main channels present into the length of the rod and microchannels disposed perpendicularly to said main channels;

applying a back pressure by an inert gas at relatively low pressure to keep the lipid solution into microchannels of the ceramic filter;

drying the lipid film onto the surface of the ceramic filter;

hydrating the lipid film; and recovering the liposomes formed during hydration in main channels of ceramic filter.

2. The process according to claim 1, wherein the ceramic filter is an asymmetric ceramic filter.

3. The process according to claim 1, wherein the ceramic filter is a symmetric ceramic filter.

4. The process according to claim 1, wherein the hydration step comprises a back-flushing of an aqueous medium and recirculation of the liposomes formed.

5. The process according to claim 1, further comprising a step of filtration and/or extrusion.

6. The process according to claim 2, wherein the asymmetric ceramic filter is a porous silicon carbide rod.

7. The process according to claim 6, wherein the porous silicon carbide rod comprises pores between 1 and 200 μm.

8. The process according to claim 6, wherein the porous silicon carbide rod comprises pores between 8 and 100 μm.

9. The process according to claim 5, wherein the filtration or extrusion step occurs on a membrane or asymmetric ceramic filter of the desired pore size.

10. Liposomes produced by the method of claim 1, which comprise a MLV liposome population.

11. A MLV liposome population according to claim 10, comprising between 80 and 99.9% of liposomes having an average mean diameter size between 0.1 and 5 μm.

12. The MLV liposome population produced by the method of claim 8, wherein the liposomes comprise hydrophilic and/or lipophilic active ingredients.

* * * * *